United States Patent [19]
Conte et al.

[11] Patent Number: 5,422,123
[45] Date of Patent: Jun. 6, 1995

[54] TABLETS WITH CONTROLLED-RATE RELEASE OF ACTIVE SUBSTANCES

[75] Inventors: Ubaldo Conte, Busto Arsizio; Aldo La Manna; Paolo Colombo, both of Pavia, all of Italy

[73] Assignee: Jagotec AG, Hergiswil, Switzerland

[21] Appl. No.: 123,982

[22] Filed: Sep. 21, 1993

Related U.S. Application Data

[63] Continuation of Ser. No. 926,380, Aug. 10, 1992, abandoned, which is a continuation of Ser. No. 620,577, Dec. 3, 1990, abandoned.

[30] Foreign Application Priority Data

Dec. 14, 1989 [IT]  Italy .................................. 22694/89

[51] Int. Cl.$^6$ ............................ A61K 9/36; A61K 9/32
[52] U.S. Cl. ................................. 424/479; 424/480; 424/482
[58] Field of Search ................ 424/78.17, 471–473, 424/479–480, 482–483

[56] References Cited

U.S. PATENT DOCUMENTS

| | | | |
|---|---|---|---|
| 4,218,433 | 8/1980 | Kooichi et al. | 424/482 |
| 4,839,177 | 6/1989 | Colombo et al. | 424/470 |
| 4,865,849 | 9/1989 | Conte et al. | 424/466 |
| 4,892,742 | 1/1990 | Shah | 424/482 |
| 4,933,186 | 6/1990 | Ohm et al. | 424/476 |

*Primary Examiner*—Edward J. Webman
*Attorney, Agent, or Firm*—Birch, Stewart, Kolasch & Birch

[57] ABSTRACT

Tablets with zero order controlled-rate of release of the active substances, consisting of a core of defined geometrical form containing the active substance, polymer substances which swell on contact with aqueous liquids and polymer substances with gelling properties, and a support applied to said core to partly cover its surface, the support consisting of polymer substances which are slowly soluble and/or slowly gellable in aqueous liquids, plasticizing substances, and possibly substances with an adjuvant function.

13 Claims, 1 Drawing Sheet

TABLETS WITH CONTROLLED-RATE RELEASE OF ACTIVE SUBSTANCES

This application is a continuation of application Ser. No. 07/926,380, filed on Aug. 10, 1992, now abandoned, which is a continuation of Ser. No. 07/620,577 filed on Dec. 3, 1990, now abandoned.

PRIOR ART

The controlled-rate release of active substances contained in tablets has been the subject of numerous studies and proposals particularly in recent years.

Important technical progress, mainly of interest to the pharmaceutical sector, was achieved with the development of a type of tablet allowing the constant controlled-rate release in accordance with zero order kinetics of substances both soluble and little soluble in water or aqueous liquids, as described in U.S. Pat. No. 4,839,177.

Said patent claims a tablet consisting of:
a) a cope comprising an active substance and having a geometrically defined form;
b) an insoluble support applied to said core to partly cover its surface and characterised in that the said core contains, in mixture with the active substance, a polymer material undergoing a high degree of swelling after contact with water or aqueous liquids and a gellable polymer material, which polymer materials can be replaced by a single polymer material having swelling and gelling properties, together with other adjuvant substances able to give the mixture suitable characteristics for its compression and acceptance of water, said support consisting of a polymer material insoluble in aqueous liquids.

The examples and information given in said patent clearly indicate that the basic characteristic of the support applied to a part of said core is its insolubility in aqueous liquids.

The tablets of said patent have however the drawback of requiring the use of solutions of polymer materials in organic solvents for applying the support, these solutions being difficult to evaporate and possibly leaving solvent traces in the pharmaceutical form, and in addition the tablets cannot be produced by the methods, procedures and equipment normally used in the tablet production industry.

In addition the rigid support can result in cracking and sometimes flaking before the active substance has been completely released.

SUMMARY

We have now discovered a new type of tablet with constant controlled-rate release of active substances in accordance with zero order kinetics, which obviates the drawbacks of tablets of the known art.

The tablets according to the present invention consist of:
a core of defined geometrical form containing the active substance, polymer substances which swell on contact with aqueous liquids, substances with gelling properties, and possibly other substances with an adjuvant function, and
a support applied to said core to partly cover its surface, and are characterised in that said support consists of polymer substances which are slowly soluble and/or slowly gellable in aqueous liquids, plasticizing substances, and possibly other substances with an adjuvant function, which plasticizing action can also be performed by said polymer substances.

These tablets can be produced industrially using the already used technology and methods, and in addition they have the advantage that the support remains intact until the complete release of the active substance.

DETAILED DESCRIPTION OF THE INVENTION

Figure 1:
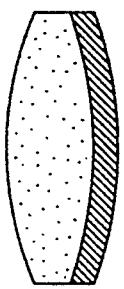
FIGS. 1-5 show tablets with core and support.

The characteristics and advantages of the tablets with constant controlled-rate release (zero order kinetics) of active substances according to the present invention will be more apparent during the course of the following detailed description.

Said tablets consist of:
a core of defined geometrical form containing the active substance, polymer substances which swell on contact with aqueous liquids, substances with gelling properties, and possibly other materials with an adjuvant function, and
a support applied to said core to partly cover its surface, and consisting of polymer substances which are slowly soluble and/or slowly gellable in aqueous liquids, plasticizing substances, and substances with an adjuvant function, which plasticizing action can also be performed by said polymer substances.

The core is obtained by compressing the mixture containing the active substance under a pressure of between 1000 and 4000 kg/cm$^2$ and therefore assumes a defined geometrical form which is generally the form of a cylindrical tablet with flat, convex or concave bases as shown for example in FIGS. 1 to 5 in which the dotted part represents the core and the hatched part represents the support.

The following substances are used to prepare the core:

As polymer materials which swell on contact with aqueous liquids, essentially insoluble polymers are used such as crosslinked sodium carboxymethylcellulose, crosslinked hydroxypropylcellulose, high molecular weight hydroxypropylmethylcellulose, carboxymethyl starch, potassium methacrylate/divinylbenzene copolymer, polymethylmethacrylate, crosslinked polyvinylpyrrolidone, high molecular weight polyvinylalcohols etc. Gellable polymer materials include methylcellulose, carboxymethylcellulose, low molecular weight hydroxypropylmethylcellulose, low molecular weight polyvinylalcohols, polyethylene glycols, non-crosslinked polyvinylpyrrolidone. Polymers which possess both swelling and gelling properties such as medium viscosity hydroxypropylmethylcellulose and medium viscosity polyvinylalcohols can also be used. Adjuvant substances include mannitol, ethylcellulose, magnesium stearate, colloidal silica and others.

The ratio of polymer substances with swelling properties to gellable polymer substances is between 1:9 and 9:1. The active substance content in the core varies with the type of substance and can be from 1 to 95% by weight.

The support has a thickness of between 10 microns and 3–4 mm depending on the hydrophilic characteristics of the components, its task being to limit and define the direction of release of the active substance contained in the cope.

In this respect, as the support is generally less hydrophilic than the core and does not contain active substance, the transfer of active substance can occur to a significant and immediate extent only from that portion of the cope which is not covered by the support.

The following substances are used to prepare the support.

The polymer substances slowly soluble and/or slowly gellable in aqueous liquids, these substances being used either alone or in mixture with each other, are chosen from the group consisting of hydroxypropylmethylcellulose having a molecular weight of between 4,000 and 2,000,000, high molecular weight carboxyvinylpolymers, polyvinylalcohols, scleroglucans, acrylates, methacrylates, hydroxypropylcellulose, sodium carboxymethylcellulose and hydrophilic cellulose derivatives.

These polymer substances represent a quantity of between 2 and 95 weight % and preferably between 30 and 90 weight % of the support composition.

The support formulation also includes substances able to provide elasticity, such as polyethylene glycols, castor oil, hydrogenated castor oil, ethyl phthalate, butyl phthalate, and natural, synthetic and semisynthetic glycerides.

These substances represent a quantity of between zero and 50 weight % and preferably between 2 and 15 weight % of the support composition.

This ensures correct release kinetics, determined by the fact that the support is sufficiently elastic to follow any change consequent on the hydration of the core without causing cracking or gaps which would result in total release of the active substance.

Finally, the support formulation includes adjuvant substances acting as binders such as polyvinylpyrrolidone, methylcellulose, ethylcellulose, gum arabic, alginic acid and its derivatives, adjuvants acting as hydrophilic agents such as mannitol, lactose, starch, colloidal silica, and adjuvants acting as hydrophobic agents such as hydrogenated castor oil, magnesium stearate, fatty substances, waxes, and natural and synthetic glycerides.

These substances represent a quantity of between zero and 50 weight and preferably between 0.5 and 35 weight % of the support composition.

By adding hydrophilic and hydrophobic agents the hydrophilic properties of the chosen support can be suitably regulated on the basis of the characteristics of the active substance and the desired release rate.

The material fop the support is prepared by mixing the constituent substances, possibly wetting with a binding solution in accordance with the known art, then bringing the mixture to the dry granular state.

Said material is given the necessary characteristics by screening and mixing with other components until an easily flowable homogeneous mixture is obtained.

Said material is applied to the core as a surface layer by using presses.

Figure 2:
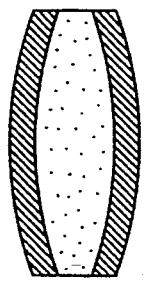
Figure 3:
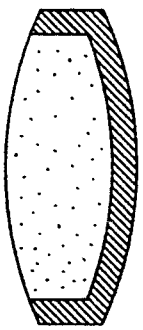
Figure 4:
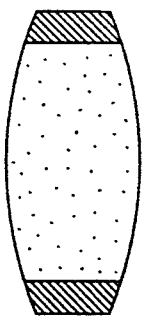
Figure 5:
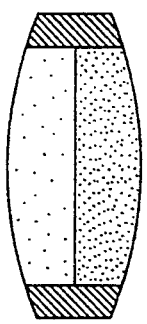

The support can be applied to one or two bases of the core as shown in FIGS. 1 and 2 respectively, or can be applied to the entire core surface with the exception of one base as shown in FIG. 3, or to the entire lateral surface with the exclusion of the two bases as shown in FIGS. 4 and 5. The support is applied using a pressure of between 1000 and 4000 kg/cm$^2$.

The following examples ape given as non-limiting illustration of the invention.

EXAMPLE 1 a—Preparation of the core granulate

The following materials were used in the indicated quantities to prepare 100,000 cores:

| | |
|---|---|
| Diltiazem (Fermion) | 4.500 kg |
| Hydroxypropylmethylcellulose (Methocel K 100 M-Colorcon) | 3.500 kg |
| Mannitol (USP grade - Carlo Erba) | 1.000 kg |
| Ethylcellulose | 0.375 kg |
| Magnesium stearate | 0.100 kg |
| Colloidal silica (Syloid 244 - Grace) | 0.100 kg |
| 95° ethanol | 7.500 liters |

The diltiazem was mixed intimately with the mannitol and hydroxypropylcellulose in a suitable mixer. A solution of ethylcellulose in 95° ethanol was prepared separately and used to wet the previously formed powder mixture. The homogeneous mass obtained in this manner was forced through an 800 micron grid and then dried to obtain a granulate which was passed through a 420 micron grid. The granulate obtained was mixed with the magnesium stearate and the colloidal silica in a suitable mixer, to obtain the granulate A1, which was white in color.

b—Preparation of the support granulate

For forming 200,000 supports a granulate of the following

| | |
|---|---|
| Hydroxypropylmethylcellulose (Methocel K 100 M-Colorcon) | 12.084 kg |
| Hydrogenated castor oil (Cutina HR - Henkel) | 1.976 kg |
| Ethylcellulose (Ethocel standard 20 - Dow Chem.) | 0.760 kg |
| Yellow iron oxide pigment (Sicopharm - Gelb 10 - BASF) | 0.152 kg |
| Colloidal silica (Syloid 244 - Grace) | 0.076 kg |
| Magnesium stearate (USP grade - Carlo Erba) | 0.152 kg |

The hydroxypropylmethylcellulose, hydrogenated castor oil and yellow iron oxide pigment were mixed in a suitable mixer and the mixture obtained was wetted with a solution of ethylcellulose in ethanol (7.6 liters of a 10% solution). The mass was then forced through an 800 micron grid, and after drying in an air circulation oven to constant weight the granulate obtained was passed through a 420 micron grid, the magnesium stearate and colloidal silica added and the system mixed for 20 minutes to obtain an easily flowable homogeneous mixture of yellow brown color and defined as the granulate B1.

c—Preparation of tablets with applied support c1—Tablets with support applied to one face (see FIG. 1):

To prepare the tablets a layer press (Manesty, Liverpool) able to produce multi-layer tablets was used. In this specific case the machine was adjusted to produce two-layer tablets, ie a layer containing the core and a second layer consisting of the support. The machine was fitted with circular dies of 7.0 mm diameter and flat punches. The first loading hopper was filled with the granulate A1 (core), the chamber depth being adjusted to contain 96.0 mg of granulate, equivalent to 45 mg of active principle. The second loading hopper was filled with the granulate B1 (support) and the machine adjusted to deliver 38 mg of granulate, this quantity being sufficient to form on said core a continuous layer of about 0.5–0.8 mm thickness after compression.

The working pressure was adjusted to about 2500–3000 kg/cm². This procedure resulted in two-layer tablets consisting of a white layer (core) containing the active principle and a yellow-brown layer (support).

The tablet production was continuous at an hourly production rate of about 45–50,000 tablets.

c2—Tablets with support applied to two faces (see FIG. 2):

To prepare tablets comprising a core with two faces covered by the support the previously described press (Manesty layer press) was used, adjusted to form three-layer tablets. As in the previous case the machine was fitted with flat cylindrical punches of 7.00 mm diameter.

The first and third loading hopper were filled with said granulate B1 (support) whereas the second hopper was filled with the granulate A1 (core). The machine was adjusted to deliver 38 mg of granulate B1 in each of stations 1 and 3, and 96 mg of granulate A1 (equivalent to 45 mg of active principle) in station 2.

Operating in accordance with the known art and adjusting the compression force to about 3000 kg/cm², three-layer tablets were produced consisting of two yellow-brown layers (support) and an intermediate white layer (core) as shown in FIG. 2.

The tablet production was continuous with an hourly production rate of 35–40,000 tablets.

Tests to determine the "in vitro" release of the active substance from the tablets prepared in Example 1

The "in vitro" release tests were conducted on the tablets complete with support as obtained by the procedure described in Example 1. For comparison purposes identical control tests were conducted on tablets consisting of cores equal to those of Example 1 but with impermeable insoluble supports obtained by partial film coating using the method of U.S. Pat. No. 4,839,177.

To better evaluate the influence of the support on the release kinetics of the active principle control tests were also carried out on the release from cores without supports.

The dissolution apparatus of USP XXI was used for the tests (paddle at 100 rpm) with 900 ml of distilled water at 37° C. as the dissolution fluid.

The results given below represent the mean of six repeat tests.

Release of diltiazem from the core without support (for comparison):

| Time (min) | total fraction released |
| --- | --- |
| 30 | 0.27 |
| 60 | 0.39 |
| 120 | 0.57 |
| 180 | 0.72 |
| 240 | 0.83 |
| 360 | 0.86 |

Release of diltiazem from the tablet comprising an impermeable insoluble support applied by partial film coating (manual) on a single face (for comparison):

| Time (min) | total fraction released |
| --- | --- |
| 30 | 0.22 |
| 60 | 0.34 |
| 120 | 0.51 |
| 180 | 0.66 |
| 240 | 0.77 |
| 360 | 0.94 |

At the end of the test the support shows cracking and flaking.

Release of diltiazem from the tablet comprising a support applied to one face by compression (Example 1 -$C_1$):

| Time (min) | total fraction released |
| --- | --- |
| 30 | 0.21 |
| 60 | 0.33 |
| 120 | 0.50 |
| 180 | 0.64 |
| 240 | 0.75 |

At the end of the test the support is unimpaired.

Release of diltiazem from the tablet comprising an impermeable insoluble support applied by partial film coating (manual) on two faces (for comparison):

| Time (min) | total fraction released |
| --- | --- |
| 60 | 0.25 |
| 120 | 0.41 |
| 180 | 0.56 |
| 240 | 0.68 |
| 300 | 0.78 |
| 360 | 0.86 |

At the end of the test the support shows cracking and flaking.

Release of diltiazem from the tablet comprising a support applied to two faces by compression (Example 1 -$C_2$):

| Time (min) | total fraction released |
| --- | --- |
| 60 | 0.21 |
| 120 | 0.39 |
| 180 | 0.53 |
| 240 | 0.66 |
| 300 | 0.76 |
| 360 | 0.85 |

At the end of the test the support is unimpaired.

EXAMPLE 2 a—Preparation of the core granulate

The following materials were used in the indicated quantities to prepare 25,000 cores:

| | |
| --- | --- |
| Diltiazem (Fermion) | 4.500 kg |
| Hydroxypropylmethylcellulose (Methocel K 100 M-Colorcon) | 0.960 kg |
| Mannitol (USP grade - Carlo Erba) | 3.450 kg |
| Ethylcellulose (Ethocel standard 20 - Dow Chem.) | 0.450 kg |
| Magnesium stearate | 0.100 kg |
| Colloidal silica (Syloid 244 - Grace) | 0.100 kg |
| 95° ethanol | 7.500 liters |

The diltiazem was mixed intimately with the mannitol and hydroxypropylcellulose in a suitable mixer. A solution of ethylcellulose in 95° ethanol was prepared separately and used to wet the previously formed powder mixture. The homogeneous mass obtained in this manner was forced through an 800 micron grid and then dried to obtain a granulate which was passed through a 420 micron grid. The granulate obtained was mixed with the magnesium stearate and the colloidal silica in a suitable mixer, to obtain the granulate A2, which was white in color.

b—Preparation of the support granulate

For forming 100,000 supports a granulate of the following composition was prepared:

| | |
|---|---|
| Hydroxypropylmethylcellulose (Methocel K 100 M-Colorcon) | 11.92 kg |
| Hydrogenated castor oil (Cutina HR - Henkel) | 1.95 kg |
| Ethylcellulose (Ethocel standard 20 - Dow Chem.) | 0.75 kg |
| Yellow iron oxide pigment (Sicopharm - Gelb 10 - BASF) | 0.150 kg |
| Colloidal silica (Syloid 244 - Grace) | 0.075 kg |
| Magnesium stearate (USP grade - Carlo Erba) | 0.150 kg |
| Ethanol | 7.50 liters |

The hydroxypropylmethylcellulose, hydrogenated castor oil and yellow iron oxide pigment were mixed in a suitable mixer and the mixture obtained was wetted with a solution of ethylcellulose in ethanol (7.5 liters of a 10% solution). The mass was then forced through an 800 micron grid, and after drying in an air circulation oven to constant weight the granulate obtained was passed through a 420 micron grid, the magnesium stearate and colloidal silica added and the system mixed for 20 minutes to obtain an easily flowable homogeneous mixture defined as the granulate B2 of yellow-brown color.

c—Preparation of tablets with applied support $c_1$-Tablets with support applied to one face (see FIG. 1):

To prepare the tablets a layer press (Manesty, Liverpool) able to produce multi-layer tablets was used. In this specific case the machine was adjusted to produce two-layer tablets, ie a layer containing the core and a second layer consisting of the support. The machine was fitted with circular dies of 11.0 mm diameter and flat punches. The first loading hopper was filled with the granulate A2 (core), the chamber depth being adjusted to contain 384 mg of granulate (equivalent to 180 mg of active principle). The second loading hopper was filled with the granulate B2 (support) and the machine adjusted to deliver 75 mg of granulate, this quantity being sufficient to form on said core a continuous layer of about 1 mm thickness after compression.

The working pressure was adjusted to about 2500–3000 kg/cm$^2$. This procedure resulted in two-layer tablets consisting of a white layer (core) containing the active principle and a yellow-brown layer (support).

The tablet production was continuous at an hourly production rate of about 45–50,000 tablets.

$c_2$—Tablets with support applied to two faces (see FIG. 2):

To prepare tablets comprising a core with two faces covered by the support the previously described press (Manesty layer press) was used, adjusted to form three-layer tablets. As in the previous case the machine was fitted with flat cylindrical punches of 11.0 mm diameter.

The first and third loading hopper were filled with said granulate B2 (support) whereas the second hopper was filled with the granulate A2 (core). The machine was adjusted to deliver 75 mg of granulate B2 in each of stations 1 and 3, and 384 mg of granulate A2 (equivalent to 180 mg of active principle) in station 2. Operating in accordance with the known art and adjusting the compression force to about 3000 kg/cm$^2$, three-layer tablets were produced consisting of two yellow-brown layers (support) and an intermediate white layer (core) as shown in FIG. 2.

The tablet production was continuous with an hourly production rate of 30–35,000 tablets.

Tests to determine the "in vitro" release of the active substance from the tablets prepared in Example 2

The "in vitro" release tests were conducted on the tablets complete with support as obtained by the procedure described in Example 2. To better evaluate the influence of the support on the release kinetics of the active principle, control tests were also carried out on the release from cores formed from granulate A2 and having an identical composition and thus an equal diltiazem content (180 mg) and with the same geometrical form (11.0 mm diameter) but without a support.

The dissolution apparatus of USP XXI was used fop the tests (paddle at 100 rpm) with 900 ml of distilled water at 37° C. as the dissolution fluid.

The results given below represent the mean of six repeat tests.

Release of diltiazem from the core without support (for comparison):

| Time (min) | total fraction released |
|---|---|
| 30 | 0.18 |
| 60 | 0.32 |
| 120 | 0.51 |
| 180 | 0.65 |
| 240 | 0.80 |

Release of diltiazem from the tablet comprising a support applied to one face:

| Time (min) | total fraction released |
|---|---|
| 30 | 0.13 |
| 60 | 0.20 |
| 120 | 0.32 |
| 180 | 0.39 |
| 240 | 0.43 |
| 360 | 0.57 |
| 480 | 0.70 |
| 600 | 0.82 |

Release of diltiazem from the tablet comprising a support applied to two faces:

| Time (min) | total fraction released |
|---|---|
| 60 | 0.13 |
| 120 | 0.20 |
| 240 | 0.33 |
| 360 | 0.42 |
| 480 | 0.55 |
| 600 | 0.72 |

EXAMPLE 3 a—Preparation of the core granulate

The following materials were used in the indicated quantities to prepare 100,000 cores:

| | |
|---|---|
| Verapamil HCl (Recordati - Milan) | 4.000 kg |
| Hydroxypropylmethylcellulose (Methocel K 100 M-Colorcon) | 3.500 kg |
| Mannitol (USP grade - Carlo Erba) | 1.500 kg |
| Ethylcellulose | 0.325 kg |
| Magnesium stearate | 0.100 kg |
| Colloidal silica (Syloid 244 - Grace) | 0.100 kg |
| Ethanol-chloroform (5:1) | 7.500 liters |

The Verapamil HCl was mixed intimately with the mannitol and hydroxypropylcellulose in a suitable mixer. A solution of ethylcellulose in ethanol:-chloroform (5:1) was prepared separately and used to wet the previously formed powder mixture. The homogeneous mass obtained in this manner was forced through an 800 micron grid and then dried to obtain a granulate which was passed through a 420 micron grid. The granulate obtained was mixed with the magnesium stearate and the colloidal silica in a suitable mixer, to obtain the granulate A3, which was white in color.

b—Preparation of the support granulate

For forming 200,000 supports a granulate of the following composition was prepared:

| | |
|---|---|
| Hydroxypropylmethylcellulose (Methocel K 100 M-Colorcon) | 12.000 kg |
| Hydrogenated castor oil (Cutina HR - Henkel) | 3.200 kg |
| Polyvinylpyrrolidone (USP grade - Prodotti Gianni, Milan) | 0.760 kg |
| Yellow FCF aluminum lake (Colorcon, Orpington UK) | 0.152 kg |
| Colloidal silica (Syloid 244 - Grace) | 0.076 kg |
| Magnesium stearate (USP grade - Carlo Erba) | 0.152 kg |
| 95° ethanol | 6.500 liters |

The hydroxypropylmethylcellulose, hydrogenated castor oil and dye were mixed in a suitable mixer and the mixture obtained was wetted with a solution of polyvinylpyrrolidone in ethanol. The mass was then forced through an 800 micron grid, and after drying in an air circulation oven to constant weight the granulate obtained was passed through a 420 micron grid, the magnesium stearate and colloidal silica added and the system mixed for 20 minutes to obtain an easily flowable homogeneous mixture of bright yellow-brown color and defined as the granulate B3.

c—Preparation of tablets with applied support c1—Tablets with support applied to one face (see FIG. 1):

To prepare the tablets a layer press (Manesty, Liverpool) able to produce multi-layer tablets was used. In this specific case the machine was adjusted to produce two-layer tablets, ie a layer containing the core and a second layer consisting of the support. The machine was fitted with circular dies of 7.0 mm diameter and flat punches. The first loading hopper was filled with the granulate A3 (core), the chamber depth being adjusted to contain 95.25 mg of granulate (equivalent to 40 mg of Verapamil hydrochloride).

The second loading hopper was filled with the granulate B3 (support) and the machine adjusted to deliver 40 mg of granulate, this quantity being sufficient to form on said core a continuous layer of about 1 mm thickness after compression.

The working pressure was adjusted to about 2500–3000 kg/cm$^2$. Two-layer tablets were obtained consisting of a white layer (core) containing the active principle and a yellow-brown layer (support). The tablet production was continuous at an hourly production rate of about 45,000–50,000 tablets.

c2—Tablets with support applied to two faces (see FIG. 2):

To prepare tablets comprising a core with two faces covered by the support the previously described press (Manesty layer press) was used, adjusted to form three-layer tablets. As in the previous case the machine was fitted with flat cylindrical punches of 7.00 mm diameter.

The first and third loading hopper were filled with said granulate B3 (support) whereas the second hopper was filled with the granulate A3 (core). The machine was adjusted to deliver 40 mg of granulate B3 in each of stations 1 and 3, and 95.25 mg of granulate A3 (equivalent to 40 mg of verapamil hydrochloride) in station 2. Operating in accordance with the known art and adjusting the compression force to about 3000 kg/cm$^2$, three-layer tablets were produced consisting of two yellow-brown layers (support) and an intermediate white layer (core).

The tablet production was continuous with an hourly production rate of 35–40,000 tablets.

Tests to determine the "in vitro" release of the active substance from the tablets prepared in Example 3

The "in vitro" release tests were conducted on the tablets complete with support as obtained by the procedure described in Example 3. For comparison Purposes identical control tests were conducted on tablets containing an identical quantity of active principle but with the support obtained by partial film coating using the method or U.S. Pat. No. 4,839,177.

To better evaluate the influence of the support on the release kinetics of the active principle, control tests were also carried out on the release from cores having an identical composition, the same geometrical form and containing the same quantity of Verapamil hydrochloride, but without supports.

The dissolution apparatus of USP XXI was used for the tests (paddle at 100 rpm) with 1000 ml of distilled water at 37° C. as the dissolution fluid.

For the tests, three identical tablets prepared as described were inserted in known manner into a hard gelatin capsule (type Coni-Supro Capsugel), each final pharmaceutical form thus containing 120 mg of Verapamil hydrochloride.

The results given below represent the mean of six repeat tests.

Release of Verapamil HCl from cores without support (for comparison):

| Time (min) | total fraction released |
|---|---|
| 30 | 0.13 |
| 60 | 0.19 |
| 120 | 0.38 |
| 180 | 0.53 |
| 240 | 0.63 |
| 300 | 0.72 |

Release of Verapamil HCl from tablets comprising an impermeable water-insoluble support applied by partial film coating on one face (for comparison):

| Time (min) | total fraction released |
|---|---|
| 30 | 0.07 |
| 60 | 0.12 |

-continued

| Time (min) | total fraction released |
| --- | --- |
| 120 | 0.21 |
| 180 | 0.28 |
| 240 | 0.37 |
| 360 | 0.50 |
| 480 | 0.62 |

Release of Verapamil HCl from tablets comprising a permeable hydrophilic support applied to one face in accordance with the procedures of the present invention:

| Time (min) | total fraction released |
| --- | --- |
| 30 | 0.07 |
| 60 | 0.13 |
| 120 | 0.20 |
| 180 | 0.29 |
| 240 | 0.39 |
| 360 | 0.53 |
| 480 | 0.68 |

Release of Verapamil HCl from the tablets comprising an impermeable insoluble support applied by partial film coating on two faces (for comparison):

| Time (min) | total fraction released |
| --- | --- |
| 60 | 0.07 |
| 120 | 0.12 |
| 180 | 0.18 |
| 240 | 0.24 |
| 360 | 0.37 |
| 480 | 0.45 |
| 600 | 0.58 |

Release of Verapamil HCl from the tablets comprising a permeable hydrophilic support applied to two faces by compression in accordance with the procedures of the present invention:

| Time (min) | total fraction released |
| --- | --- |
| 60 | 0.07 |
| 120 | 0.13 |
| 180 | 0.19 |
| 240 | 0.26 |
| 360 | 0.38 |
| 480 | 0.48 |
| 600 | 0.62 |

EXAMPLE 4

Preparation of tablets with the support applied to the entire surface with the exception of one face in accordance with FIG. 3.

The tablets were prepared using a Manesty Drycota machine (Manesty, Liverpool) consisting of two rotary presses connected together via a transfer system. In this machine the first press produces the cores, the transfer system allowing the cores to be continuously withdrawn and positioned on the surface of the lower punches of the second rotary press, exactly centered with respect to the dies. This second press is used to apply the support by compression. In this specific case the first press was fitted with flat circular punches and dies of 10.0 mm diameter, the loading hopper was filled with granulate A1 obtained as in Example 1 and the depth of the filling chamber was adjusted so that it contained 256 mg of granulate A1, corresponding to 120 mg of active principle. Thus cores of 10.0 mm diameter and an average weight of 256 mg were obtained from the first press. The working pressure was adjusted to about 1500–2000 kg/cm$^2$.

The second press was fitted with flat circular punches and dies of 13.0 mm diameter. The filling hopper of the second press was filled with the granulate B1 obtained as in Example 1 and forming the support, the press being adjusted to deliver 180 mg of granulate. As the transfer system enabled the 10.0 mm cores to be positioned centrally on the lower punches and in the dies of the second press before the granulate was loaded, the indicated quantity (180 mg) of granulate B1 became distributed all around the core (within a circular ring of 1.5 mm thickness) and on the upper face, the lower face of the core being in contact with the punch surface, Regular and correct operation of the system by which the cores are transferred from the first to the second press is essential in obtaining finished tablets in which that core face not covered is exactly centered, resulting in a regular lateral support layer of uniform thickness.

The working pressure of the second press was adjusted to about 2500–3500 kg/cm$^2$.

By this procedure the cores were covered by compression on their entire surface with the exception of one face. The finished tablets had one white face (core) containing the active principle and a yellow-brown coating (support) covering the entire cope with the exception of one face.

The tablets were produced continuously at an hourly production rate of about 10–12,000 finished tablets.
Tests to determine the "in vitro" release of the active substance from the tablets prepared in Example 4

The "in vitro" release tests were conducted on the tablets complete with support as obtained by the procedure described in Example 4. For comparison purposes analogous control tests were conducted on tablets consisting of cores equal to those of Example 4 and with impermeable insoluble supports obtained by partial film coating using the method of U.S. Pat. No. 4,839,177.

To better evaluate the influence of the support on the release kinetics of the active principle control tests were also carried out on the release from cores without supports.

The dissolution apparatus of USP XXI was used for the tests (basket at 100 rpm) with 900 ml of distilled water at 37° C. as the dissolution fluid.

The results given below represent the mean of six repeat tests.

Release of diltiazem from the core without support (for comparison):

| Time (min) | total fraction released |
| --- | --- |
| 30 | 0.15 |
| 60 | 0.23 |
| 120 | 0.37 |
| 180 | 0.48 |
| 240 | 0.58 |
| 480 | 0.85 |

Release of diltiazem from the tablet comprising an impermeable insoluble support applied by partial film coating (manual) over the entire surface with the exception of one face (for comparison):

| Time (min) | total fraction released |
|---|---|
| 30 | 0.08 |
| 60 | 0.12 |
| 120 | 0.18 |
| 240 | 0.27 |
| 360 | 0.37 |
| 480 | 0.49 |
| 600 | 0.62 |
| 900 | 0.87 |

At the commencement of the dissolution test the core swells considerably, to push beyond the impermeable insoluble support; this results during the initial stage in a more rapid release of active substance than the system obtained by compression.

Release of diltiazem from the tablet comprising a support applied by compression over the entire core surface with the exception of one face, in accordance with the procedures of Example 4:

| Time (min) | total fraction released |
|---|---|
| 30 | 0.06 |
| 60 | 0.09 |
| 120 | 0.14 |
| 240 | 0.25 |
| 360 | 0.34 |
| 480 | 0.45 |
| 600 | 0.56 |
| 900 | 0.82 |

During the entire release test the support follows the swelling of the core in a regular and homogeneous manner, resulting in regular and constant release of the active substance. The release kinetics, which can be expressed by the equation:

$$y = 2.734 + 0.088x \quad (R = 1.00)$$

is a linear function of time (zero order kinetics)

We claim:

1. A system for the controlled-rate release of active substance which comprises:
    (a) a deposit-core comprising an effective amount of the active substance and having defined geometric form, and
    (b) a support-platform applied to said deposit-core, wherein said deposit-core contains at least the active substance, and at least one member selected from the group consisting of (1) a polymeric material which swells on contact with water or aqueous liquids and a gellable polymeric material wherein the ratio of the polymeric material which swells on contact with water or aqueous liquids to the gellable polymeric material is between 1:9 and 9:1, and (2) a single polymeric material having both swelling and gelling properties, and
    wherein the support-platform is an elastic support, applied to said deposit-core so it partially covers the surface of the deposit-core and follows changes due to hydration of the deposit-core and is slowly soluble and/or slowly gellable in aqueous fluids.

2. The system of claim 1, wherein said support-platform comprises a polymer substance which is slowly soluble or slowly gellable in aqueous liquids and a plasticizing substance.

3. The system as claimed in claim 2, wherein said plasticizing substance contained in said support-platform is selected from the group consisting of polyoxyethylene glycols, castor oil, hydrogenated castor oil, ethyl phthalate, butyl phthalate, natural glycerides, synthetic glycerides and semisynthetic glycerides.

4. The system as claimed in claim 3, wherein said plasticizing substance represents between 2 and 15% by weight of the support-platform.

5. The system as claimed in claim 2, wherein said support-platform comprises a substance acting as a binder selected from the group consisting of polyvinylpyrrolidone, methylcellulose, ethylcellulose, gum arabic, and alginic acid.

6. The system as claimed in claim 2, wherein said support-platform comprises a substance acting as a hydrophilic agent selected from the group consisting of mannitol, lactose, starch and colloidal silica.

7. The system as claimed in claim 2, wherein said support-platform comprises a substance acting as a hydrophobic agent selected from the group consisting of hydrogenated castor oil, magnesium stearate, a fatty substance, wax, natural glycerides and synthetic glycerides.

8. The system of claim 2, wherein the thickness of said support-platform is 0.5 to 0.8 mm.

9. The system of claim 2, wherein the thickness of said support-platform is about 1 mm.

10. The system as claimed in claim 2, wherein the support-platform remains intact until complete release of the active substance.

11. A process for preparing a system for the controlled-rate release of active substance having a deposit-core and a support-platform which comprises:
    granulating the deposit-core ingredients according to claim 2, and compressing said granular mixture to form a deposit-core of defined geometrical form; and
    screening and mixing the support-platform substances according to claim 2 to obtain an easily flowable homogeneous granular mixture and applying said easily flowable homogeneous granular mixture onto a portion of the surface of said deposit-core by compressing to form said support-platform partially covering said deposit-core of defined geometrical form, to prepare a tablet.

12. A tablet produced by the process of claim 11.

13. A system for the controlled-release of active substance which comprises:
    a deposit-core defined in geometrical form containing:
    a) an active substance in an amount between 1% and 95% of the weight of the deposit-core;
    b) a polymer substance which swells on contact with an aqueous liquid, which is selected from the group consisting of crosslinked sodium carboxymethylcellulose, crosslinked hydroxypropylcellulose, polyhydroxypropyl-methylcellulose having a molecular weight sufficiently high to result in swelling in aqueous liquids, carboxy-methyl starch, potassium methacrylate/divinylbenzene copolymer, crosslinked polyvinylpyrrolidone, and polyvinyl alcohol; and
    c) a polymeric substance with gelling properties which is selected from the group consisting of methylcellulose and non-crosslinked polyvinylpyrrolidone,
    wherein the ratio of b) to c) is between 1:9 and 9:1; and
    an elastic support-platform that follows any changes due to hydration of the deposit-core, applied to said deposit-core, which partially covers the surface of said deposit-core, wherein said support-platform comprises:

1) a polymer substance which is slowly soluble or slowly gellable in aqueous liquids which is selected from the group consisting of polyhydroxypropylmethylcellulose, polyvinyl alcohol, polyacrylate, polymethacrylate, polyhydroxypropylcellulose, and polysodium carboxymethylcellulose; and 2) a plasticizing substance selected from the group consisting of polyethylene glycol, castor oil, hydrogenated castor oil, ethyl phthalate, butyl phthalate and natural glycerides, synthetic glycerides and semisynthetic glycerides, and wherein said polymer 1) is between 30% and 90% by weight of said support-platform.

* * * * *